(12) United States Patent
Al-Hassan

(10) Patent No.: US 8,551,532 B2
(45) Date of Patent: Oct. 8, 2013

(54) METHOD OF MAKING AN ANTI-INFLAMMATORY COMPOSITION

(75) Inventor: Jassim M. Al-Hassan, Surra (KW)

(73) Assignee: Kuwait University, Safat (KW)

( * ) Notice: Subject to any disclaimer, the term of this patent is extended or adjusted under 35 U.S.C. 154(b) by 0 days.

(21) Appl. No.: 13/288,022

(22) Filed: Nov. 2, 2011

(65) Prior Publication Data

US 2013/0108705 A1    May 2, 2013

(51) Int. Cl.
*A61K 35/60* (2006.01)

(52) U.S. Cl.
USPC .......................................... 424/537; 424/520

(58) Field of Classification Search
None
See application file for complete search history.

(56) References Cited

U.S. PATENT DOCUMENTS

| | | |
|---|---|---|
| 5,658,594 A | 8/1997 | Al-Hassan |
| 5,912,018 A * | 6/1999 | Al-Hassan ................... 424/537 |
| 2007/0053955 A1 | 3/2007 | Larson et al. |
| 2007/0060651 A1 | 3/2007 | Larson et al. |
| 2009/0202497 A1 | 8/2009 | Habener et al. |
| 2009/0324636 A1 | 12/2009 | Piechocki et al. |
| 2010/0292330 A1 | 11/2010 | Pan et al. |
| 2011/0119774 A1 | 5/2011 | Zlotkin et al. |

OTHER PUBLICATIONS

Al-Hassan JM et al. Comp Biochem Physiol, 1986, 85B: 41-47.*
Gunnlaugsdottir et al. J Sci Food Agric, 61: 235-240, 1993.*
Mohri S et al. J Agric Food Chem, 40: 573-576, 1992.*
Perona JS et al. Analysis of Neutral Lipids: Triacylglycerols, in "Handbook of Food Analysis: Physical Cahracterization and Nutrient Analysis", second edition, vol. 1, 2004, p. 281.*
Tsutsui et al., A unique epidermal mucus lectin identified from catfish (*Silurus asotus*): First evidence of intelectin in fish skin slime (2011) Journal of Biochemistry, 150(5), 501-514.*
Al-Hassan et al., "Diabetic ulcer healing preparations from the skin of the Arabian Gulf catfish (*Arius bilineatus* Val.): a novel and effective treatment", *Int J Tissue React.*, 1990; 12(2):121-35.
Al-Hassan et al., "Acceleration of wound healing responses induced by preparations from the epidermal secretions of the Arabian Gulf catfish (*Arius bilineatus*, Valenciennes)," *Journal of Wilderness Medicine*, vol. 2, Issue 3, pp. 153-163, Aug. 1991.
Al-Hassan et al,, "Effects of preparations from the skin of the Arabian Gulf catfish, (*Arius bilineatus* Val.) on back pain and other related pain", *The FASEB Journal*, 2007; 21:488.1.

* cited by examiner

*Primary Examiner* — Jon P Weber
(74) *Attorney, Agent, or Firm* — Richard C. Litman

(57) ABSTRACT

In order to prepare an anti-inflammatory composition extracted from the skin of the Arabian Gulf catfish (*Arius bilineatus* (Valenciennes)), a gelatinous secretion is collected from the skin of the Arabian Gulf catfish. The gelatinous secretion is biologically active due to the presence of biologically active proteins and lipids. The lipids are extracted from the gelatinous secretion, and then are mixed into an inert dermatological cream. The inert dermatological cream serves as a carrier for the lipids. Preferably, the mixture includes approximately 0.2% to 0.8% of the lipids by weight. Either the total lipids may be used in the mixture, or the lipids, prior to mixing into the cream, may be fractionated into major lipid fractions.

19 Claims, No Drawings

METHOD OF MAKING AN ANTI-INFLAMMATORY COMPOSITION

BACKGROUND OF THE INVENTION

1. Field of the Invention

The present invention relates to anti-inflammatory compositions, and particularly to a topical anti-inflammatory composition extracted from the skin of the Arabian Gulf catfish (*Arius bilineatus* (Valenciennes)).

2. Description of the Related Art

The Arabian Gulf catfish (*Arius bilineatus* (Valenciennes)) naturally exudes an aqueous gelatinous secretion from its skin that contains proteins and lipids that are found to act as anti-inflammatory agents for back pain and other neurological disorders, as well as providing accelerated healing for wounds, ulcers and the like. By dry weight, the gelatinous secretion contains 85% proteins and 13% lipids.

However, the Arabian Gulf catfish produces venoms from its venomous spines and venom glands near its pectoral spines. Additionally, since the gelatinous secretion is exuded while the catfish is still alive, contaminants other than the venom (such as feces, vomit and blood) are also often mixed with the desired secretion. Thus, a method of preparing an anti-inflammatory composition from this gelatinous secretion solving the aforementioned problems is desired.

SUMMARY OF THE INVENTION

The method of preparing an anti-inflammatory composition uses extracts from the skin of the Arabian Gulf catfish (*Arius bilineatus* (Valenciennes)). A gelatinous secretion is first collected from the skin of the Arabian Gulf catfish. The extraction process of the gelatinous secretion may be performed by shocking the catfish (mechanically, thermally, electrically, or any other manner) to produce the secretions and then scraping the skin of the catfish to collect the secretions. Preferably, the scraping of the skin is alternated with washing of the skin of the catfish, which may take place in seawater.

The gelatinous secretion is biologically active due to the presence of the biologically active proteins and lipids contained therein. The lipids may be extracted in aqueous form or by first freeze drying the extracted gelatinous secretion and then extracting the lipids from the freeze-dried gelatinous secretion in an extraction solvent formed from chloroform and methanol in a 2:1 ratio by volume. Preferably, this application of the extraction solvent is repeated three additional times, A secondary extraction solvent may also be used, where the secondary extraction solvent is formed from chloroform, methanol and isopropanol in a 2:1:0.25 ratio by volume, and the ratio of total volume of extraction solvent to freeze dried gelatinous secretion to be extracted is approximately 3:1 by volume. The remaining freeze dried material, following lipid extraction, contains the proteins.

Alternatively, in order to obtain more of the skin material, the catfish may be skinned with a sharp blade. The skin is placed in approximately four times its volume in a 0.9% normal saline solution containing a phosphate buffer at a pH of 7. This mixture is then homogenized using a blender or the like, preferably keeping the mixture chilled with ice or the like so that the temperature does not exceed 4° C. The homogenate is then centrifuged at 5,000 RPM×g to remove the debris, and a clear solution is collected. The clear solution, which contains the extracted lipids and proteins, is then freeze dried.

For this alternate technique of lipid extraction, the lipids may be extracted using the extraction solvent(s) described above, either after partial reduction of the buffered saline by freeze drying to a moisture content, or preferably through complete removal of water followed by extraction in the solvent. The extract is collected by filtration and evaporated under reduced pressure in a rotary evaporator at 15° C. This results in a thick oily residue, which contains the total extracted lipids. This lipid mixture is then preferably kept under nitrogen, away from light, in a freezer until use. A solid material remains after lipid extraction, and this solid material contains the total protein fraction. For fractionation and purification of the protein components, using the aqueous gel starting material is preferable (i.e., the first method used in the extraction, with direct scraping of the catfish skin being used), because this method avoids denaturation of some of the protein components by the effect of the lipid extraction solvent.

Following the extraction of the lipids by either technique, the lipids extracted from the gelatinous secretion are mixed into an inert dermatological cream. The inert dermatological cream serves as a carrier for the lipids. Preferably, the cream includes approximately 0.2% to 0.8% of the lipids by weight. Either the total lipids may be used in the mixture, or the lipids, prior to mixing into the cream, may be fractionated into major lipid fractions.

As noted above, the lipids may be extracted in aqueous form or by first freeze drying the extracted gelatinous secretion and then extracting the lipids from the freeze-dried gelatinous secretion in an extraction solvent formed from chloroform and methanol in a 2:1 ratio by volume. When the original gelatinous material is freeze dried, the lipid fractions described above may be used for lipid enrichment of the original material. The enriching lipids may be a) the total extracted lipid material; b) neutral lipids only; or c) neutral lipids and phospholipids only, in a 20:1 ratio by weight. The enriching lipid fractions used for the dermatological cream preparations described above are dissolved in chloroform and methanol in a 2:1 ratio by volume, and are then added to the freeze dried material such that the added lipid fraction is 0.01% of the weight of the freeze dried protein.

The organic solvent mixture is then evaporated on a rotary evaporator at 15° C. This evaporation removes the solvents and provides thorough mixing of the total proteins and lipids. The resulting dry powder is then stored under nitrogen in a tight stoppered dark bottle until use. Just before use, a small amount of distilled water is added to the amount of the freeze dried preparation and mixed with a glass rod or spatula, which may then be applied topically to the site of inflammation and/or demyelination of the nerves. It should be understood that the lipid extraction may be used with other types of marine life, such as other species of catfish or moray eels, for example.

These and other features of the present invention will become readily apparent upon further review of the following specification.

DETAILED DESCRIPTION OF THE PREFERRED EMBODIMENTS

The method of preparing an anti-inflammatory composition uses extracts from the skin of the Arabian Gulf catfish (*Arius bilineatus* (Valenciennes)). The anti-inflammatory composition may be applied directly to the skin of a patient, and is preferably provided in the form of a topical cream or gel. A gelatinous secretion is first collected from the skin of the Arabian Gulf catfish. The Arabian Gulf catfish naturally exudes a gelatinous secretion through its skin, and this secretion may be collected while the catfish is alive. The catfish may be caught and removed from the water for approximately one to two minutes. During this time, the catfish is held by its gill cover and the gelatinous secretion, which contains proteins and lipids, may then be scraped from the skin with a blade and stored in a test tube or the like. During collection and transport, the test tube or other holder is preferably chilled by dry ice or the like. It should be understood that the lipid extraction to be described in detail below may be used with other types of marine life, such as other species of catfish or moray eels, for example. Further, it should be understood that the removal may be performed by any suitable method alternative to scraping, such as with a suction pump or the like.

Preferably, during the extraction process of the gelatinous secretion, the scraping of the skin is alternated with washing of the skin of the catfish, which may take place in seawater. The Arabian Gulf catfish releases venom as a protective measure. This venom should be washed from the skin in-between scrapings. Other contaminants, such as vomit, blood and feces, may also be removed by this washing.

The gelatinous secretion is biologically active due to the presence of the biologically active proteins and lipids contained therein. The lipids may be extracted in aqueous form or by first freeze drying the extracted gelatinous secretion, and then extracting the lipids from the freeze dried gelatinous secretion in an extraction solvent formed from chloroform and methanol in a 2:1 ratio by volume. Preferably, this application of the extraction solvent is repeated three additional times. A secondary extraction solvent may also be used, where the secondary extraction solvent is formed from chloroform, methanol and isopropanol in a 2:1:0.25 ratio by volume. The ratio of total volume of extraction solvent to the gelatinous material or the freeze dried form of it to be extracted for lipids is approximately 3:1 by volume.

Alternatively, in order to obtain more of the skin material (the lipids in particular), the catfish may be skinned with a sharp blade. The skin is placed in approximately four times its volume in a 0.9% normal saline solution containing a phosphate buffer at a pH of 7. This mixture is then homogenized using a blender or the like, preferably keeping the mixture chilled with ice or the like so that the temperature does not exceed 4° C. The homogenate is then centrifuged at 5,000 RPM×g to remove the debris, and a clear solution is collected. The clear solution, which contains the extracted lipids and proteins, is then freeze dried.

For this alternate technique of lipid extraction, the lipids may be extracted using the extraction solvent(s) described above, either after partial reduction of the buffered saline by freeze drying to reduce moisture content, or, preferably through complete removal of water and then extraction with the extraction solvent. The extract is then collected by filtration and evaporated under reduced pressure in a rotary evaporator at 15° C. This results in a thick oily residue, which contains the total extracted lipids. This lipid mixture is then preferably kept under nitrogen, away from light, in a freezer until use. A solid material remains after lipid extraction, and this solid material contains the total protein fraction. For fractionation and purification of the protein components, using the aqueous gel starting material is preferable (i.e., the first method used in the extraction, with direct scraping of the catfish skin being used), because this method avoids denaturation of some of the protein components by the effect of the lipid extraction solvent.

Following the extraction of the lipids by either technique, the lipids extracted from the gelatinous secretion are mixed into an inert dermatological cream. The inert dermatological cream serves as a carrier for the lipids. Preferably, the cream includes approximately 0.2% to 0.8% of the extracted lipids by weight. Either the total lipids may be used in the mixture, or the lipids, prior to mixing into the cream, may be fractionated into major lipid fractions.

In order to perform the fractionation, the lipid extract is loaded on a keiselgel-60 silica gel of 63-100 mesh size column, or the like, and the major lipid fractions are then eluted at a temperature of approximately 15° C. Neutral lipids are eluted in approximately 1 L of a petroleum ether and chloroform mixture having a ratio of approximately 1:1 by volume. The glycolipids are eluted in approximately 1 L of acetone. The phospholipids are eluted in approximately 1 L of methanol, followed by approximately 1 L of a chloroform and methanol mixture having a ratio of approximately 2:1 by volume to remove any residual lipid material.

Steroids may be further separated from the neutral lipid fraction (also performed at a temperature of approximately 15° C.). In order to perform the separation and purification of steroids, fractionation of the neutral lipids into three major fractions is performed using three different solvent systems, performed on a keiselgel-60 silica gel of 63-100 mesh size column or the like, and then eluted with 1 L of petroleum ether (of 40-60° C. boiling range); then eluted with 1 L of a petroleum ether and chloroform mixture at a ratio of 75:25 by volume; and then eluted with 1 L of a petroleum ether and chloroform mixture at a ratio of 1:1 by volume. Each elution produces a different fraction, which is then run through thin layer chromatography (TLC) for separation and purification of the steroids and other lipids in the fractions.

Neutral lipids fractionated from the column are spotted on TLC silica gel 60 F254 aluminum sheets (20×20 cm) for the separation and purification of the steroids. The solvent system used for the development on TLC is ethyl acetate and cyclodextrin in a 1:1 ratio by volume until the front line reaches half of the TLC plate. At this point, the polar steroids are moved from the base. The plates, following drying, are then placed in a hexane, diethyl ether and acetic acid mixture in a 30:19:1 ratio by volume, and then run until the front line reaches 1 cm below the top of the plate, such that all of the spots are resolved properly. The plates are then removed and dried for the detection of spots.

The spots are marked under ultraviolet light and are stained using 1% vanillin stain (dissolved in sulfuric acid and ethanol at a 40:10 ratio by volume. Steroids appear as violet spots after staining. The bands corresponding to the different compounds visualized under ultraviolet light and the stained compounds are then separated by scraping off the bands from the TLC plate. The separated compounds are eluted with chloroform, and the samples are collected by drying the solvent under reduced pressure in a rotary evaporator at 15° C.

As noted above, the lipids mixed into the cream may be the total extracted lipids, the neutral lipids or the phospholipids. The glycolipids may be removed. Alternatively, both the neutral lipids and the phospholipids may be mixed together into the cream.

The proteins in the gelatinous secretion are a mixture of about 50 different proteins. These are composed of soluble and insoluble fractions. Analysis of the proteins in the soluble fraction reveals a mixture of highly active biochemical and pharmacological components, with activities on both blood and cellularity. These include a plasma clotting factor that has been found to be specific to blood clotting factor X1, a hemolytic factor, platelet activating factors (PAFs) at unusually high levels (more than 5,000 times the threshold level required for normal platelet activation), and a hemagglutination factor. In addition to these, there are also vaso-active components, phosphatases, including an acid phosphatase, a general esterase and a tyrosine specific esterase, and proteins with collagenase-like activities that cleave collagen into fragments. The soluble fraction also contains a factor that activates phospholipase $A_2$, tyrosine and serine/threonine protein phosphorylase, proteolytic and antimicrobial activities, leukotrienes, interleukin 1 and growth factors that affect macrophages and pancreatic β-cells, along with four protein components that are capable of binding human fibronectin.

The lipids are a mixture of the main fractions described above. These lipids act as anti-inflammatory substances when used either as a cream, as described above, or as an enriching part of a preparation also containing the proteins. The neutral lipids include eicosanoids, cholesterol, triglycerides, fatty acids and steroids. The neutral lipids and the phospholipids, in particular, act as potent anti-inflammatory agents.

As noted above, the lipids may be extracted in aqueous form or by first freeze drying the extracted gelatinous secretion and then extracting the lipids from the freeze-dried gelatinous secretion in an extraction solvent formed from chloroform and methanol in a 2:1 ratio by volume. When the original gelatinous material is freeze dried, the lipid fractions described above may be used for lipid enrichment of the original material. The enriching lipids may be a) the total extracted lipid material; b) neutral lipids only; or c) neutral lipids and phospholipids only, in a 20:1 ratio by weight. The enriching lipid fractions used for the dermatological cream preparations described above are dissolved in chloroform and methanol in a 2:1 ratio by volume, and are then added to the freeze dried material such that the added lipid fraction is 0.01% of the weight of the freeze dried protein.

The organic solvent mixture is then evaporated on a rotary evaporator at 15° C. This evaporation removes the solvents and provides thorough mixing of the total proteins and lipids. The resulting dry powder is then stored under nitrogen in a tight stoppered dark bottle until use. Just before use, a small amount of distilled water is added to the amount of the freeze dried preparation and mixed with a glass rod or spatula until it turns into a gelatinous constituent, which may then be applied topically to the site of inflammation and/or demyelination of the nerves. It should be understood that the lipid extraction may be used with other types of marine life, such as other species of catfish or moray eels, for example.

In use, the preparation is applied topically to the patient, preferably after cleaning the affected skin or body part with alcohol. The applied preparation and inflamed body part are then covered with a non-absorbent dressing, such as a plastic film or wrap, and then left for four to six hours. The treated body part is then washed with soap and water. This treatment may then be repeated every 24 hours for two to five days, depending on the nature of the inflammation. The cream preparation may be used to treat general inflammation, inflamed nerves, inflamed soft tissues, chronic back and joint pain, inflamed discs of the vertebral column, paralysis, neuropathy, demyelinated nerves, demyelination polyneuropathy and other neurological disorders. The preparation containing the proteins may be used to treat the same ailments that the cream preparations are used to treat as well as for treating wounds, non-healing ulcers including diabetic foot ulcers with osteomyelitis, psoriasis, and erectile dysfunction.

It is to be understood that the present invention is not limited to the embodiments described above, but encompasses any and all embodiments within the scope of the following claims.

I claim:

1. A method of making an anti-inflammatory composition, comprising the steps of:
    extracting a gelatinous secretion from the skin of an Arabian Gulf catfish, the gelatinous secretion containing proteins and lipids;
    extracting the lipids from the gelatinous secretion; and
    mixing the lipids from the gelatinous secretion into a preparation to form a topical dermatological treatment composition, wherein the step of mixing the lipids from the gelatinous secretion into the preparation comprises mixing the lipids from the gelatinous secretion into an inert dermatological cream, the inert dermatological cream serving as a carrier for the lipids, the mixture including about 0.2% to 0.8% of the lipids by weight.

2. The method of making an anti-inflammatory composition as recited in claim 1, further comprising the step of freeze drying the gelatinous secretion following extraction thereof from the skin of the Arabian Gulf catfish, the lipids being extracted from the freeze dried gelatinous secretion leaving a freeze dried composition containing the proteins, the preparation being formed from the freeze dried composition.

3. The method of making an anti-inflammatory composition as recited in claim 1, wherein the step of extracting the gelatinous secretion from the skin of the Arabian Gulf catfish comprises the steps of:
    removing the skin from the Arabian Gulf catfish;
    soaking the skin in an approximately 0.9% saline solution containing a phosphate buffer so that the solution has a pH of about 7, the volume of the solution being about four times the volume of the skin;
    homogenizing the skin and the solution by blending at a temperature up to about 4° C. to form a homogenized mixture;
    centrifuging the homogenized mixture to separate out a clear solution containing the lipids and the proteins;
    removing water from the clear solution to form a gelatinous material containing the lipids and the proteins; and
    extracting the lipids from the gelatinous material in an extraction solvent formed from chloroform and methanol in a 2:1 ratio by volume.

4. The method of making an anti-inflammatory composition as recited in claim 3, wherein the step of extracting the lipids from the gelatinous secretion further comprises repeating the application of the extraction solvent three additional times.

5. The method of making an anti-inflammatory composition as recited in claim 4, wherein the step of extracting the lipids from the gelatinous secretion further comprises the step of extracting the lipids from the freeze dried gelatinous secretion in a secondary extraction solvent formed from chloroform, methanol and isopropanol in a 2:1:0.25 ratio by volume, the ratio of total volume of extraction solvent to the freeze dried gelatinous secretion to be extracted for the lipids being about 3:1 by volume.

6. The method of making an anti-inflammatory composition as recited in claim 3, further comprising the step of fractionating the extracted lipids into major lipid fractions.

7. The method of making an anti-inflammatory composition as recited in claim 6, wherein the step of fractionating the extracted lipids into major lipid fractions comprises the steps of:
    eluting neutral lipids in about 1 L of a petroleum ether and chloroform mixture having a ratio of approximately 1:1 by volume;
    eluting glycolipids in about 1 L of acetone; and eluting phospholipids in about 1 L of methanol followed by about 1 L of a chloroform and methanol mixture having a ratio of approximately 2:1 by volume.

8. The method of making an anti-inflammatory composition as recited in claim 7, further comprising the step of removing the glycolipids and the phospholipids, leaving the neutral lipids, prior to the step of mixing the lipids into the inert dermatological cream.

9. The method of making an anti-inflammatory composition as recited in claim 7, further comprising the step of removing the glycolipids, leaving the neutral lipids and the phospholipids, prior to the step of mixing the lipids into the inert dermatological cream.

10. The method of making an anti-inflammatory composition as recited in claim 7, further comprising the step of separation of steroids from the neutral lipid fraction.

11. A method of making an anti-inflammatory composition, comprising the steps of
    extracting a gelatinous secretion from the skin of an Arabian Gulf catfish, the gelatinous secretion containing proteins and lipids, wherein the step of extracting the gelatinous secretion further comprises the steps of
        scraping an exterior surface of the skin from a live Arabian Gulf catfish and storing the gelatinous secretion;
        cooling the stored gelatinous secretion; and
        alternately washing the skin of the Arabian Gulf catfish and scraping the exterior surface of the skin;
    extracting the lipids from the gelatinous secretion; and
    mixing the lipids from the gelatinous secretion into a preparation to form a topical dermatological treatment composition.

12. The method of making an anti-inflammatory composition as recited in claim 11, wherein the step of extracting the lipids from the gelatinous secretion comprises extracting the lipids in aqueous form.

13. The method of making an anti-inflammatory composition as recited in claim 11, wherein the step of extracting the lipids from the gelatinous secretion comprises the steps of:
    freeze drying the gelatinous secretion; and
    extracting the lipids from the freeze dried gelatinous secretion in an extraction solvent formed from chloroform and methanol in a 2:1 ratio by volume.

14. The method of making an anti-inflammatory composition as recited in claim 13, wherein the step of extracting the lipids from the gelatinous secretion further comprises repeating the application of the extraction solvent three additional times.

15. The method of making an anti-inflammatory composition as recited in claim 13, wherein the step of extracting the lipids from the gelatinous secretion further comprises the step of extracting the lipids from the freeze dried gelatinous secretion in a secondary extraction solvent formed from chloroform, methanol and isopropanol in a 2:1:0.25 ratio by volume, the ratio of total volume of extraction solvent to lipids to be extracted being about 3:1 by volume.

16. The method of making an anti-inflammatory composition as recited in claim 13, further comprising the step of fractionating the extracted lipids into major lipid fractions.

17. The method of making an anti-inflammatory composition as recited in claim 16, wherein the step of fractionating the extracted lipids into major lipid fractions comprises the steps of:
    eluting neutral lipids in about 1 L of a petroleum ether and chloroform mixture having a ratio of approximately 1:1 by volume;
    eluting glycolipids in about 1 L of acetone; and
    eluting phospholipids in about 1 L of methanol followed by about 1 L of a chloroform and methanol mixture having a ratio of approximately 2:1 by volume.

18. The method of making an anti-inflammatory composition as recited in claim 17, further comprising the step of removing the glycolipids and the phospholipids prior to the step of mixing the lipids into the inert dermatological cream.

19. The method of making an anti-inflammatory composition as recited in claim 17, further comprising the step of removing the glycolipids prior to the step of mixing the lipids into the inert dermatological cream.

* * * * *